US 6,458,076 B1
Oct. 1, 2002

(54) MULTI-LUMEN MEDICAL DEVICE

(75) Inventor: David L. Pruitt, Union City, CA (US)

(73) Assignee: 5 Star Medical, San Jose, CA (US)

( * ) Notice: Subject to any disclaimer, the term of this patent is extended or adjusted under 35 U.S.C. 154(b) by 0 days.

(21) Appl. No.: 09/495,810

(22) Filed: Feb. 1, 2000

(51) Int. Cl.$^7$ ................................................ A61B 1/00
(52) U.S. Cl. ........................ 600/146; 600/139; 600/128
(58) Field of Search ................................ 600/139, 153, 600/146, 128, 130, 129; 604/523, 524, 164.09

(56) References Cited

U.S. PATENT DOCUMENTS

| | | | |
|---|---|---|---|
| 4,392,485 A | | 7/1983 | Hiltebrandt |
| 4,580,551 A | * | 4/1986 | Siegmund et al. ............. 128/4 |
| 4,706,656 A | | 11/1987 | Kuboto |
| 4,784,144 A | | 11/1988 | Ono et al. |
| 4,872,740 A | | 10/1989 | Terada et al. |
| 4,892,099 A | | 1/1990 | Ohkawa et al. |
| 4,911,148 A | | 3/1990 | Sosnowski et al. |
| 4,919,112 A | * | 4/1990 | Siegmund ...................... 128/4 |
| 4,947,827 A | * | 8/1990 | Opie et al. ..................... 128/4 |
| 5,140,975 A | * | 8/1992 | Krauter .......................... 128/4 |
| 5,188,092 A | | 2/1993 | White |
| 5,241,970 A | | 9/1993 | Johlin, Jr. et al. |
| 5,307,803 A | | 5/1994 | Matsuura et al. |
| 5,320,602 A | | 6/1994 | Karpiel |
| 5,325,845 A | | 7/1994 | Adair |
| 5,341,240 A | | 8/1994 | Broome |
| 5,397,302 A | | 3/1995 | Weaver et al. |
| 5,398,687 A | | 3/1995 | Abell |
| 5,416,638 A | | 5/1995 | Broome |
| 5,458,112 A | | 10/1995 | Weaver |
| 5,483,951 A | * | 1/1996 | Frassica et al. ............. 600/104 |
| 5,519,532 A | | 5/1996 | Broome |
| 5,549,542 A | | 8/1996 | Kovalcheck |
| 5,555,131 A | | 9/1996 | Horton |
| 5,599,299 A | | 2/1997 | Weaver et al. |
| 5,704,899 A | * | 1/1998 | Milo .......................... 600/161 |
| 5,779,624 A | | 7/1998 | Chang |
| 5,788,681 A | | 8/1998 | Weaver et al. |
| 5,834,214 A | | 11/1998 | Iovanna et al. |
| 5,843,028 A | | 12/1998 | Weaver et al. |
| 5,892,630 A | | 4/1999 | Broome |
| 5,916,147 A | * | 6/1999 | Boury .......................... 600/146 |
| 5,938,585 A | | 8/1999 | Donofrio |
| 5,960,145 A | * | 9/1999 | Sanchez ...................... 385/116 |
| 6,010,449 A | * | 1/2000 | Selmon et al. .............. 600/117 |
| 6,013,024 A | * | 1/2000 | Mitsuda et al. ............. 600/146 |
| 6,099,485 A | | 8/2000 | Patterson |
| 6,146,389 A | | 11/2000 | Geitz |
| 6,213,974 B1 | * | 4/2001 | Smith et al. ............. 604/95.01 |
| 6,217,510 B1 | | 4/2001 | Ozawa et al. |
| 6,277,065 B1 | | 8/2001 | Donofrio |

FOREIGN PATENT DOCUMENTS

| | | |
|---|---|---|
| WO | WO 91/15793 | 10/1991 |
| WO | WO 93/15647 | 8/1993 |
| WO | WO 98/01074 | 1/1998 |
| WO | WO 00/54653 | 9/2000 |

* cited by examiner

Primary Examiner—Linda C. M. Dvorak
Assistant Examiner—Jocelyn Ram
(74) Attorney, Agent, or Firm—Burns Doane Swecker & Mathis, L.L.P.

(57) ABSTRACT

A multi-lumen medical device such as an endoscope or a catheter includes a shaft and a distal tip which are formed as multi-lumen extrusions having a large central working channel and a plurality of surrounding auxiliary lumens. The auxiliary lumens are arranged around the central working channel in a uniform manner so that the flexibility of the extruded member is uniform in a plurality of different directions. Use of the multi-lumen extrusion for the medical device provides a balanced device with a flexibility which is substantially the same in all directions. The medical device may be provided with four way tip deflection by providing four pull wires within four of the auxiliary lumens.

21 Claims, 2 Drawing Sheets

MULTI-LUMEN MEDICAL DEVICE

BACKGROUND OF THE INVENTION

1. Field of the Invention

The invention relates to a multi-lumen medical device, and more particularly, the invention relates to an extruded multi-lumen medical device, such as an endoscope or a catheter, with a steerable tip.

2. Brief Description of the Related Art

Endoscopes are extensively used in the medical field to perform surgical, therapeutic, diagnostic, or other medical procedures under direct visualization. Conventional endoscopes generally contain several endoscope components such as fiberoptic light guides, a fiberoptic image guide, and a working channel. These components are positioned in the lumen of a sheathing tube of the endoscope. Examples of know endoscope designs are shown in U.S. Pat. Nos. 4,706,656; 4,911,148; and 5,704,899.

Steerable endoscopes include an elongated shaft and a flexible distal tip. The flexible tip is deflectable by moving pull wires with controls located on an endoscope handle at the proximal end of the device. When the endoscope is provided with one pull wire, the tip is deflectable in one direction and when two pull wires are provided, the tip is deflectable in two directions. In use, the one way and two way deflectable endoscopes are manipulated to reach a desired location by both deflecting the tip and rotating the entire device from the proximal end. However, rotation of the entire endoscope by the user to steer the tip is undesirable because it is difficult for the user, requires high torqueability of the endoscope shaft, and causes high stress on the endoscope shaft.

Accordingly, it would be desirable to provide a medical device with four way tip deflection for improved maneuverability and precision.

It would also be desirable to provide a medical device with a centrally located working lumen for a balanced device which bends uniformly in different directions.

It would also be desirable to provide a medical device which is inexpensively formed by extruding a multi-lumen flexible shaft.

SUMMARY OF THE INVENTION

The present invention relates to a medical device formed from a multi-lumen extrusion with a central lumen and a plurality of surrounding lumens.

In accordance with one aspect of the present invention, an endoscope with four way tip deflection includes an extruded multi-lumen shaft with a central lumen and a plurality of surrounding lumens, and an extruded multi-lumen tip with a central lumen and a plurality of surrounding lumens. The tip is connected to a distal end of the shaft and the tip is more flexible than the shaft. Four pull wires extend through the plurality of surrounding lumens of the shaft and the tip. An endoscope handle is connectable to a proximal end of the shaft and the pull wires. The handle has controls for four way tip deflection.

In accordance with an additional aspect of the present invention, a multi-lumen steerable medical device includes an extruded multi-lumen shaft with a central lumen and a plurality of surrounding lumens arranged around the central lumen in a symmetrical pattern, and an extruded multi-lumen tip connected to a distal end of the shaft. The tip has a central lumen and a plurality of surrounding lumens arranged around the central lumen in a symmetrical pattern. The tip is more flexible than the shaft. A plurality of pull wires extend through the surrounding lumens of the shaft and the tip.

In accordance with a further aspect of the invention, an endoscope includes a multi-lumen extrusion having a central operating channel and a plurality of auxiliary channels surrounding the central operating channel in a symmetrical pattern. A plurality of light guides extend through some of the plurality of auxiliary channels and a plurality of pull wires extend through others of the plurality of auxiliary channels.

The present invention provides advantages of a four way deflectable multilumen medical device.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
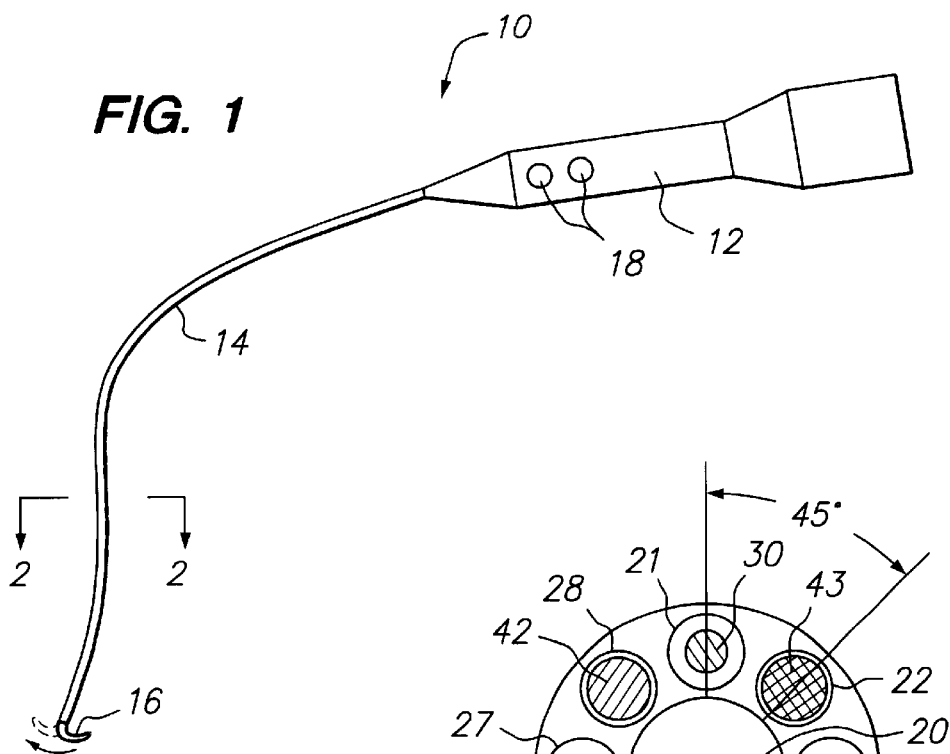
FIG. 1 is schematic side view of an endoscope according to the present invention.
Figure 2:
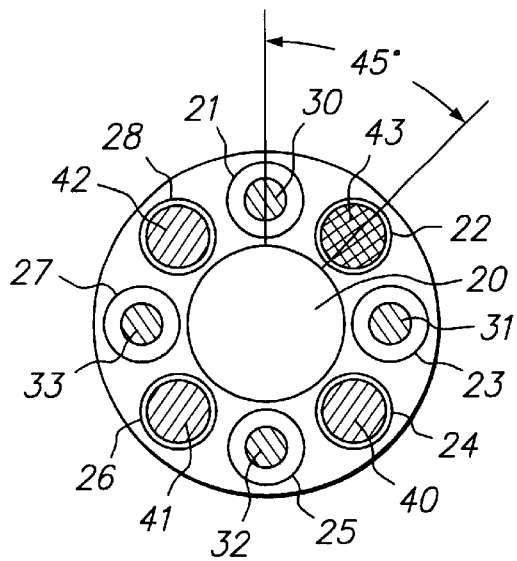
FIG. 2 is a cross sectional view taken along line 2—2 of FIG. 1.
Figure 3:
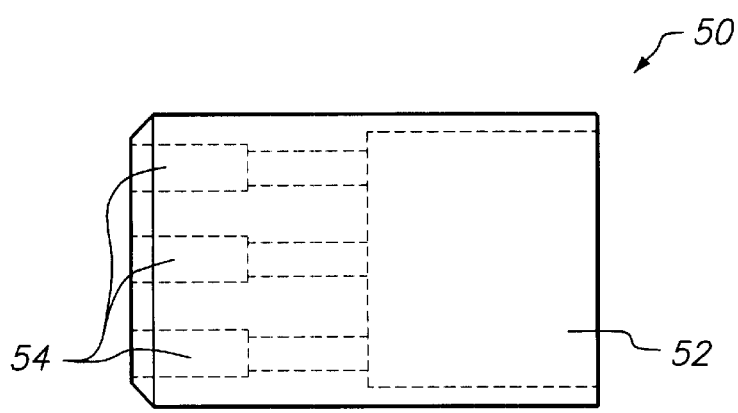
FIG. 3 is a side view of an end cap for the endoscope of FIG. 1.

FIGS. 1–3 illustrate one embodiment of an endoscope according to the present invention. The endoscope 10 includes a handle 12, a shaft 14, and a distal tip 16. The shaft 14 and distal tip 16 of the endoscope are both multi-lumen extrusions having identical or substantially identical cross sections. The shaft 14 and tip 16 are joined together in any known manner, such as by adhesive, ultrasonic welding, or the like, to form the working portion of the endoscope. The distal tip 16 is formed of a material which is more flexible than the shaft 14. The flexibility of the distal tip 14 allows the tip of the endoscope to be steerable. The endoscope handle 12 has controls 18, such as dials or levers, for control of the distal tip 16 and preferably receives a camera for visualization.

As shown in FIG. 2, the shaft 14 and distal tip 16 each include a large central lumen 20 and a plurality of auxiliary lumens 21–28. The central lumen 20 is used as a working channel for performing a medical procedure such as a surgical procedure, drug delivery, tissue sampling, or the like. The auxiliary lumens 21–28 are used for auxiliary functions such as steering, illumination, visualization, irrigation, suction, and the like.

According to one embodiment of the endoscope 10, four of the auxiliary lumens 21, 23, 25, and 27 receive pull wires 30–33 which are used to provide four way tip deflection. The auxiliary lumens 24, 26, and 28 receive light guides 40, 41, and 42 for illumination of a tissue site and the auxiliary lumen 22 receives an image guide 43 for visualization. The pull wires and light guides are secured at the distal end of the endoscope by an end cap 50 such as the end cap illustrated in FIG. 3. The end cap 50 has a central bore 52 which receives the end of the distal tip 16. The end cap also has a plurality of bores 54 for securing the pull wires and light guides.

The use of a multi-lumen extrusion with a central working lumen 20 and uniformly distributed auxiliary lumens 21–28 provides a balanced device with a flexibility which is substantially the same in all directions. This balanced device has a distal tip 16 which bends uniformly in four directions for better tip control than known endoscopes of this size or of similar size. The multi-lumen extruded endoscope is less expensive than known endoscopes with multiple conduits in a single outer sheath. In addition, the four way tip deflection provides increased endoscope life because the shaft does not have to be rotated during use causing stress on the shaft. The central channel is also less prone to collapse in the multi-lumen extrusion than in a conventional endoscope because of the uniform wall thickness.

The extruded shaft 14 and distal tip 16 of the present invention are sized based on the particular medical application. The endoscope according to the present invention may be any one of the know endoscopes, such as a neonatal broncoscope, pediatric bronchoscope, intubation scope, pediatric cystoscope, ureteroscope, ureterorenalscope, choledochoscope, nephroscope, hysteroscope, thoracoscope, arthroscope, sinuscope, otoscope, laparoscope, ERCP accessory scope, and the like. The endoscope may also be used in veterinary and industrial applications.

Although the invention will be described in detail with reference to an endoscope, the steerable medical device according to the present invention may be an endoscope, a catheter, or like medical device. The catheters according to the invention are similar to the endoscopes without light or image guides for direct visualization. The auxiliary lumens which are used for light guides in the endoscope may be eliminated in the catheter, may be left vacant, or may be used as separate auxiliary channels.

Figure 4:
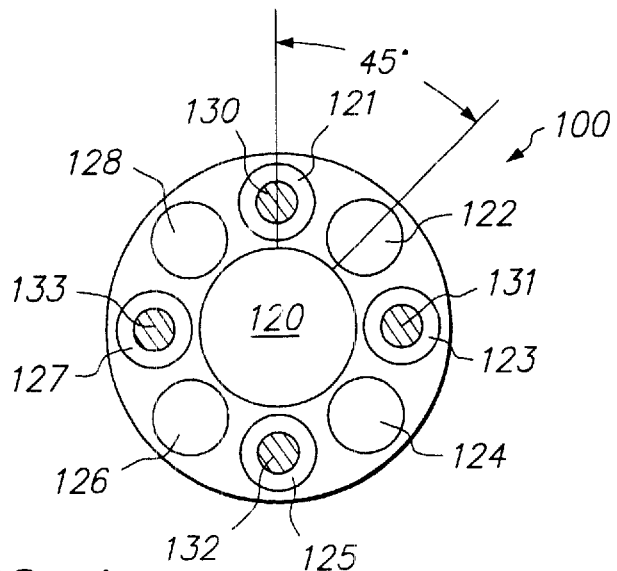
FIG. 4 is a cross sectional view of a catheter according to the present invention.

FIG. 4 is a cross section of a catheter shaft 100 having a central lumen 120 and a plurality of surrounding auxiliary lumens 121–128. The auxiliary lumens 121, 123, 125, and 127 contain pull wires 130–133 for control of the distal tip. As shown in FIG. 4, the auxiliary lumens 122, 124, 126, and 128 are left vacant. Alternatively, the auxiliary lumens 122, 124, 126, and 128 may be used as secondary channels for irrigation, evacuation, drug delivery, or other functions. The catheters of the present invention are used under indirect visualization techniques such as fluoroscopy.

Figure 5:
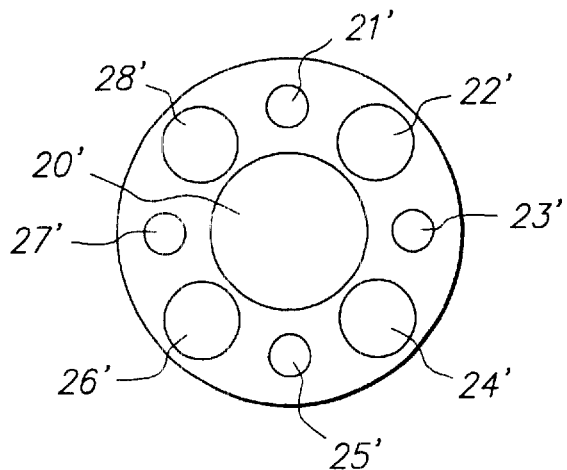
FIG. 5 is a cross sectional view of an alternative embodiment of an extrusion for use in the present invention.
Figure 6:
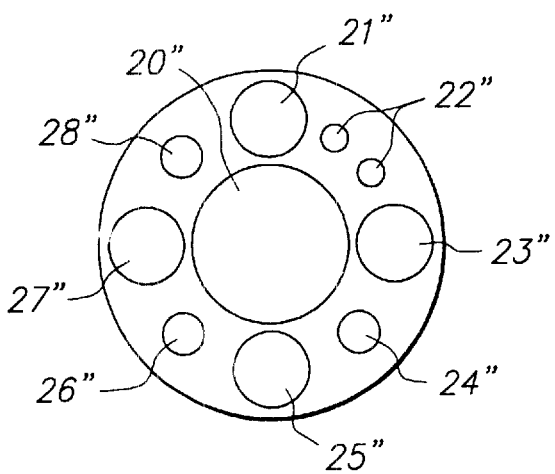
FIG. 6 is a cross sectional view of another alternative embodiment of an extrusion for use in the present invention.

FIGS. 5–6 illustrate alternative embodiments of extrusions for forming the medical devices according to the present invention. In FIG. 5, the auxiliary lumens 21'–28' are formed in two different sizes. The smaller auxiliary lumens 21', 23', 25', and 27' are provided for the pull wires while the larger auxiliary lumens 22', 24', 26', and 28' are provided for illumination and visualization light pipes.

FIG. 6 illustrates an alternative embodiment of an extrusion in which one auxiliary lumens is replaced with two smaller auxiliary lumens 22". These two smaller auxiliary lumens 22" are sized so that the flexibility of the extrusion is maintained uniform in all directions. The central lumen 20" and auxiliary lumens 21", 23"–28" remain as in the embodiment of FIG. 5.

The extruded shaft and tip of the medical device according to the present invention are preferably formed of an engineering thermoplastic elastomer, such as PEBAX. Other materials which may be used include Nylon 11 and Hytrel. The material used for the shaft portion 14 of the medical device preferably has a hardness of about 50D or greater. The material used for the flexible tip 16 preferably has a hardness of about 30D to about 45D, or preferably about 40D. Preferably, the material has a softening point greater than about 276° F. so that the device does not deform during autoclaving. Alternatively, if a material with a low softening point is used, one or more mandrels may be inserted into the open lumens of the extrusion during sterilization.

The medical device according to the present invention has an outer diameter of about 10 mm or less and an inner diameter of about 1–5 mm. The auxiliary lumens have diameters of about 0.1–5 mm. Preferably, the medical device of the present invention has an outer diameter of about 2.5–6 mm, an inner diameter of about 1.0–2.5 mm, and auxiliary lumen diameters of about 0.3–1.5 mm. The tip 16 preferably has a length of about 1–4 cm depending on the tip curvature required. The length of the shaft 14 will vary greatly depending on the application.

The fiberoptic light pipes 40–43 for use in the present invention are conventional glass or plastic light fibers which are sized as appropriate for the space available. The pull wires 30–33 are any of the pull wires which are known in the art such as single strand or multi-strand stainless steel or titanium wires.

According to a preferred embodiment of the invention, the extruded multi-lumen shaft 14 and tip 16 are reinforced to provide column strength and to allow flexibility and articulation of the tip. The reinforcement may be any of the known reinforcements such as stainless steel wire reinforcement which may be positioned at the inner diameter, at the outer diameter, embedded within the wall, or within the lumens of the extruded multi-lumen shaft and tip. According to one example of the invention, a stainless steel braided wire reinforcement layer is positioned along the walls of the central lumen of the extrusion and is coated to prevent the wire reinforcement from contacting on instruments which are inserted through the central lumen.

The following are five examples of endoscope size configurations for use in different medical applications. The medical applications listed are merely examples of some of the applications for which a particular size may be useful.

EXAMPLE 1

An endoscope having a 2.6 mm outer diameter, a 1.1 mm inner diameter, and 0.5 mm diameter auxiliary lumens may be used as a neonatal broncoscope, pediatric cysto scope, arthroscope, sinuscope, or nephro scope.

EXAMPLE 2

An endoscope having a 3.2–3.4 mm outer diameter, a 1.35 mm inner diameter, and 0.5 mm diameter auxiliary lumens may be used as a pediatric broncoscope, intubation scope, ureteroscope, choledochoscope, arthroscope, otoscope, or laparoscope.

EXAMPLE 3

An endoscope having a 4.0–4.2 mm outer diameter, a 2 mm inner diameter, and 0.5 mm diameter auxiliary lumens may be used as an intubation scope, a nephroscope, thoracoscope, otoscope, or laparoscope.

EXAMPLE 4

An endoscope having a 5–5.5 mm outer diameter, a 2–2.5 mm inner diameter, and 1 mm diameter auxiliary lumens may be used as a laparscope.

EXAMPLE 5

An endoscope having a 2 mm outer diameter, a 0.5 mm inner diameter, and 0.5 mm diameter auxiliary lumens may be used as a neonatal bronoscope, pediatric cystoscope, ureterorenal scope, or choledochoscope.

The above-examples have been provided as merely illustrative of the size and corresponding functions of some of the endoscopes according to present invention. The multi-lumen extrusions for use in the present invention preferably are extruded with tolerances of about ±001" or less.

Although the present invention describes a flexible endoscope, the invention may also be used to form a rigid endoscope by the addition of a rigid tube such as a stainless steel tube positioned around the shaft portion of endoscope.

While the invention has been described in detail with reference to the preferred embodiments thereof, it will be apparent to one skilled in the art that various changes and modifications can be made and equivalents employed, without departing from the present invention.

What is claimed is:

1. An endoscope with four way tip deflection comprising:

an extruded multi-lumen shaft with a central lumen and a plurality of surrounding lumens;

an extruded multi-lumen tip wiht a central lumen and a plurality of surrounding lumens, the tip connected to a distal end of the shaft, and the tip is more flexible than the shaft, wherein the extruded multi-lumen shaft and the extruded multi-lumen tip are each extruded as a single piece with the central lumen and surrounding lumens;

four pull wires extending through the plurality of surrounding lumens of the shaft and the tip; and an endoscope handle connectable to a proximal end of the shaft and the pull wires, the handle having controls for four way tip deflection.

2. The endoscope of claim 1, wherein the plurality of surrounding lumens include four lumens containing the four pull wires and four lumens for visualization optics.

3. The endoscope of claim 2, wherein the visualization optics are fixed in the four lumens.

4. The endoscope of claim 1, wherein the multi-lumen shaft has an outer diameter of 6 mm or less.

5. The endoscope of claim 1, wherein the plurality of surrounding lumens all have substantially the same diameter.

6. The endoscope of claim 1, wherein the plurality of surrounding lumens are spaced substantially evenly around the central lumen.

7. The endoscope of claim 1, wherein at least one of the plurality of surrounding lumens is left open.

8. The endoscope of claim 1, wherein the plurality of surrounding lumens are positioned around the central lumen in a pattern which provides the shaft and tip with substantially uniform flexibility in a plurality of directions.

9. The endoscope of claim 1, wherein the central lumen of the shaft and tip is an open working channel.

10. A multi-lumen steerable medical device comprising:

an extruded multi-lumen shaft with a central lumen and a plurality of surrounding lumens arranged around the central lumen in a symmetrical pattern;

an extruded multi-lumen tip connected to a distal end of the shaft, the tip having a central lumen and a plurality of surrounding lumens arranged around the central lumen in a symmetrical pattern, the tip is more flexible than the shaft, wherein the extruded multi-lumen shaft and the extruded multi-lumen tip are each extruded as a single piece with the central lumen and surrounding lumens; and a plurality of pull wires extending through the surrounding lumens of the shaft and the tip.

11. The medical device of claim 10, wherein the plurality of surrounding lumens include four lumens containing four pull wires.

12. The medical device of claim 11, wherein some of the plurality of surrounding lumens contain visualization optics.

13. The medical device of claim 10, further comprising visualization optics positioned in some of the plurality of surrounding lumens.

14. The medical device of claim 10, wherein the plurality of surrounding lumens all have substantially the same diameter.

15. The medical device of claim 14, wherein the plurality of surrounding lumens are spaced substantially evenly around the central lumen.

16. The medical device of claim 10, further comprising the stainless steel woven wire reinforcement located in or on the shaft and tip to provide column strength to the medical device.

17. The medical device of claim 8, wherein the extruded multi-lumen shaft has an outer diameter of 6 mm or less.

18. The medical device of claim 8, wherein the central lumen is an open working channel.

19. A method of forming an endoscope comprising:

extruding a multi-lumen shaft as a single piece having a central lumen and a plurality of auxiliary lumens surrounding the central lumen;

extruding a multi-lumen tip as a single piece having a central lumen and a plurality of auxiliary lumens surrounding the central lumen, wherein the tip is more flexible than the shaft;

connecting the tip to a distal end of the shaft;

inserting a plurality of pull wires in some of the auxiliary lumens of the shaft and tip; and inserting a plurality of optical light fibers or image fibers in others of the plurality of auxiliary lumens of the shaft and tip.

20. The method of claim 19, wherein the auxiliary lumens are arranged in a substantially symmetrical pattern about the central lumen.

21. The method of claim 19, wherein the pull wires and the optical light fibers or image fibers are inserted in an alternating arrangement in the auxiliary lumens.

* * * * *